(12) United States Patent
Hensley et al.

(10) Patent No.: US 7,799,050 B2
(45) Date of Patent: Sep. 21, 2010

(54) DEVICES AND METHODS FOR MAGNETICALLY MANIPULATING INTRAVASCULAR DEVICES

(75) Inventors: Joseph Hensley, Minneapolis, MN (US); Thomas E. Broome, Shakopee, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1143 days.

(21) Appl. No.: 10/838,988

(22) Filed: May 5, 2004

(65) Prior Publication Data

US 2005/0251197 A1 Nov. 10, 2005

(51) Int. Cl.
*A61M 29/00* (2006.01)

(52) U.S. Cl. .................................................. 606/200

(58) Field of Classification Search ............... 606/200, 606/108, 191–198, 113, 106, 110, 114, 127, 606/129, 159, 205–209; 623/1.11, 1.12; 604/104–107, 912; 128/831, 840; 166/301, 166/99, 98; 600/7; 607/128
See application file for complete search history.

(56) References Cited

U.S. PATENT DOCUMENTS

| | | | | |
|---|---|---|---|---|
| 4,619,246 A | * | 10/1986 | Molgaard-Nielsen et al. .... | 128/899 |
| 4,865,030 A | * | 9/1989 | Polyak ....................... | 606/108 |
| 5,324,304 A | * | 6/1994 | Rasmussen ................. | 606/200 |
| 5,464,023 A | * | 11/1995 | Viera ......................... | 600/585 |
| 5,570,701 A | * | 11/1996 | Ellis et al. .................... | 600/585 |
| 5,658,302 A | * | 8/1997 | Wicherski et al. ........... | 606/159 |
| 5,814,064 A | | 9/1998 | Daniel et al. | |
| 5,827,324 A | | 10/1998 | Cassell et al. | |
| 5,848,964 A | * | 12/1998 | Samuels ...................... | 600/200 |
| 5,910,154 A | | 6/1999 | Tsugita et al. | |
| 5,928,261 A | * | 7/1999 | Ruiz ........................... | 606/200 |
| 5,941,896 A | | 8/1999 | Kerr | |
| 5,984,947 A | | 11/1999 | Smith | |
| 5,989,281 A | | 11/1999 | Barbut et al. | |
| 6,001,118 A | | 12/1999 | Daniel et al. | |
| 6,013,038 A | * | 1/2000 | Pflueger ....................... | 600/585 |
| 6,059,814 A | | 5/2000 | Ladd | |
| 6,079,413 A | * | 6/2000 | Baran ...................... | 128/207.14 |
| 6,142,987 A | | 11/2000 | Tsugita | |
| 6,152,946 A | | 11/2000 | Broome et al. | |
| 6,179,859 B1 | | 1/2001 | Bates et al. | |

(Continued)

OTHER PUBLICATIONS

*UI Researchers Investigate the Use of Magnetic Treat Prostate Cancer,* UI Health Care News: Week of Feb. 19, 2001, http://www.uihealthcare.com/news/news/2001/02/19prostatecancer.html, Jan. 22, 2004, 3 pages.

(Continued)

*Primary Examiner*—(Jackie) Tan-Uyen T Ho
*Assistant Examiner*—Elizabeth Houston
(74) *Attorney, Agent, or Firm*—Crompton, Seager & Tufte, LLC

(57) ABSTRACT

Devices and methods for magnetically centering and retrieving intravascular devices within a body lumen are disclosed. An intravascular filter in accordance with an illustrative embodiment may comprise an expandable filter structure having at least one magnetic element formed therein. The intravascular filter can be retrieved using a magnetic retrieval device that includes a magnetic retrieval mechanism for centering and retrieving the intravascular filter.

18 Claims, 15 Drawing Sheets

U.S. PATENT DOCUMENTS

| | | |
|---|---|---|
| 6,217,600 B1 | 4/2001 | DiMatteo |
| 6,264,672 B1 | 7/2001 | Fisher |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,344,049 B1 | 2/2002 | Levinson et al. |
| 6,368,338 B1 * | 4/2002 | Konya et al. .................. 606/200 |
| 6,371,971 B1 * | 4/2002 | Tsugita et al. ................ 606/200 |
| 6,511,497 B1 | 1/2003 | Braun et al. |
| 6,544,276 B1 | 4/2003 | Azizi |
| 6,558,349 B1 * | 5/2003 | Kirkman .................... 604/104 |
| 6,616,680 B1 | 9/2003 | Thielen |
| 6,623,450 B1 | 9/2003 | Dutta |
| 6,656,199 B1 * | 12/2003 | Lafontaine .................. 606/191 |
| 6,689,119 B1 * | 2/2004 | Di Caprio et al. ............ 604/523 |
| 7,144,408 B2 * | 12/2006 | Keegan et al. ............... 606/200 |
| 7,232,462 B2 * | 6/2007 | Schaeffer .................. 623/11.11 |
| 2002/0183782 A1 | 12/2002 | Tsugita et al. |
| 2003/0171770 A1 | 9/2003 | Kusleika et al. |
| 2003/0187474 A1 | 10/2003 | Keegan et al. |
| 2004/0158274 A1 * | 8/2004 | WasDyke ................... 606/200 |

OTHER PUBLICATIONS

*Classes of Magnetic Materials,* Hitchhiker's Guide to Magnetism, http://www.geo.umn.edu/orgs/lrm/hg2m/hg2m_b/hg2m_b.html, Feb. 6, 2004, 10 pages.

Pokhodnya et al., *Thin Film V[TCNE], Magnets, Abstract,* http://www.chem.utah.edu/chemistry/faculty/miller/abstracts/abstract18.htm, Mar. 4, 2004, 1 page.

\* cited by examiner

DEVICES AND METHODS FOR MAGNETICALLY MANIPULATING INTRAVASCULAR DEVICES

FIELD OF THE INVENTION

The present invention relates generally to devices and methods for manipulating intravascular devices within the body. More specifically, the present invention pertains to devices and associated methods for magnetically centering and retrieving intravascular filters within a body lumen.

BACKGROUND OF THE INVENTION

Intravascular filters are used in combination with other thrombolytic agents to treat pulmonary embolism occurring within a patient. Such devices are generally inserted intravenously into a target location of the body (e.g. an artery or vein), and function by capturing blood clots (emboli) contained in the blood stream before they can reach the heart or lungs and cause permanent damage to the body. In the treatment of Deep Vein Thrombosis (DVT), for example, such filters are placed in the inferior vena cava to prevent further blood clotting in the large veins of the lower body. Placement of the filter is typically accomplished percutaneously via the femoral arteries or the jugular vein using a local anesthetic, or by performing a laparotomy with the patient under general anesthesia.

A delivery device such as a sheath or catheter may be used to transport the filter in a collapsed position through the vasculature. In certain designs, the filter can be configured to self-expand when removed from within the delivery device, allowing the filter to automatically deploy within the body. A needle, hook, barb, prong, wedge or other anchoring means disposed on the filter can be used to secure the filter to the vessel wall.

The ability to effectively retrieve the filter is dependent in part on the positioning of the filter within the blood vessel. In some situations, the filter may become offset or tilted if not properly aligned within the blood vessel as it is ejected from the delivery device, causing the filter to asymmetrically engage the vessel wall. Tilting or skewing may also occur within the blood vessel as a result of interference with the delivery and/or retrieval device, or as a result of fluctuations in the vessel wall. Such tilting or skewing can make retrieval more difficult, in some cases requiring additional steps and/or precautions be taken during implantation and subsequent retrieval.

SUMMARY OF THE INVENTION

The present invention pertains to devices and associated methods for magnetically centering and retrieving intravascular filters within a body lumen. An illustrative intravascular filter in accordance with the present invention may include an apical head and a plurality of elongated filter legs biased to expand from a substantially straight position when radially constrained within a delivery device, to an outswept position when deployed in a blood vessel. The apical head may include a magnetic element that can be used to magnetically center and retrieve the intravascular filter within the blood vessel. In certain embodiments, for example, the magnetic element may comprise a bar magnet, magnetic ring, solenoid, or other such component incorporated into or otherwise forming the apical head. In some embodiments, the magnetic element may comprise a permanent magnetic formed from a ferromagnetic material such as Neodymium-Iron-Boron (NdFeB), with a high Remanence and a Curie temperatures higher than that of body temperature. In other embodiments, the magnetic element may comprise an electromagnetic element that can be selectively energized to produce a magnetic field at certain discrete time periods during the procedure.

The present invention is further directed to a magnetic retrieval device and associated methods of use. In one illustrative embodiment, the magnetic retrieval device may include an elongated sheath and magnetic retrieval mechanism that can be used to center and retrieve an intravascular device within a blood vessel. The magnetic retrieval mechanism may include an elongated member slidably disposed within an interior lumen of the sheath. One or more magnetic elements coupled to or formed integrally with the elongated member can be employed to produce a magnetic field having a strength sufficient to detach the intravascular device from the vessel wall (if necessary) and retract it within the interior lumen of the sheath. An optional locking mechanism can be provided to secure the intravascular device to the magnetic retrieval device during the retrieval process, if desired.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
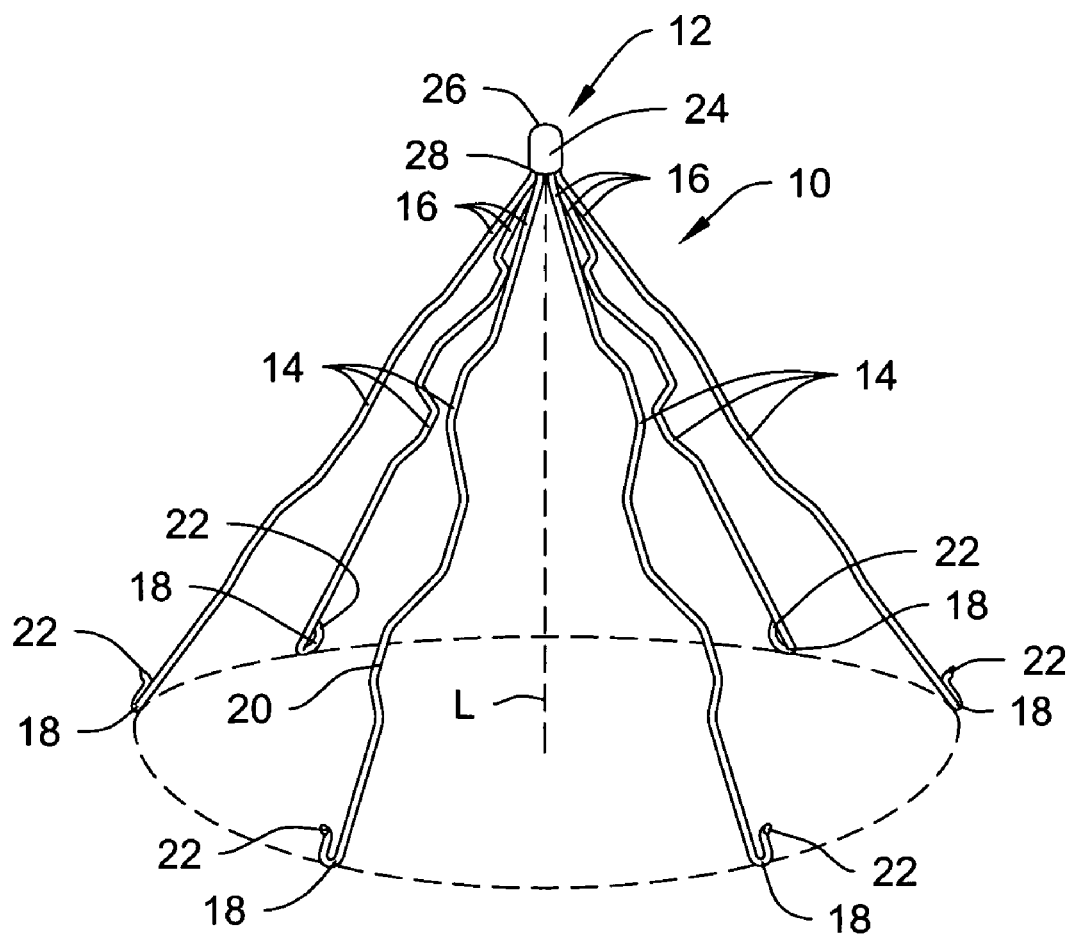
FIG. 1 is a perspective view of an intravascular filter in accordance with an illustrative embodiment of the present invention.

FIG. 1 is a perspective view of a magnetically retrievable intravascular filter 10 in accordance with an illustrative embodiment of the present invention. Intravascular filter 10, illustratively a vena cava filter, includes an apical head 12, and a plurality of elongated filter legs 14 each having a proximal section 16 and a distal section 18. Each of the filter legs 14 may be configured identically with respect to each other, and may be symmetrically spaced about a central longitudinal axis L in a generally conical-shaped configuration when expanded. The filter legs 14 may be collectively arranged about the longitudinal axis L such that the proximal section 16 of each filter leg 14 converges at the apical head 12 to form an apex. The filter legs 14 may be biased to expand from a substantially straight position when radially constrained within a delivery device to an outswept position when deployed in a blood vessel.

The filter legs 14 can be formed from a metal such as platinum, gold, tantalum, tungsten, titanium, or a metal alloy such as stainless steel (e.g. type 316L), Beta III Titanium, cobalt-chrome alloy, Elgiloy, L605, MP35N, Ta-10W, 17-4PH, or Aeromet 100. Metallic glasses such as Vitreloy 1 or Vitreloy 105 including extrinsic metal, ceramic, and/or nanoceramic fibers or particles can also be used. In certain embodiments, the filter legs 14 can be formed from a shape-memory material such as nickel-titanium alloy (Nitinol). A slight outward bend can be imparted to each filter leg 14 by heating the alloy beyond its final austenitic temperature, and then bending each filter leg 14 to a pre-defined shape. The filter legs 14 can be configured to revert to their pre-defined (i.e. bent) shape at or near body temperature (37° C.), allowing each individual filter leg 14 to maintain a straight position until deployed in the blood vessel. Also using this technique, one or more bend regions 20 can be formed on each of the filter legs 14 to increase the total surface area of the intravascular filter 10. If desired, the filter legs 14 can include an anti-thrombogenic coating such as herapin (or its derivatives), urokinase, or PPack (dextrophenylalanine proline arginine chloromethylketone) to prevent insertion site thrombosis.

As can be seen in an expanded position in FIG. 1, the filter legs 14 may be configured to extend outwardly away from the apical head 12 to permit the intravascular filter 10 to be anchored along the inner wall of a blood vessel. In certain embodiments, the distal section 18 of each filter leg 14 may include an anchoring member 22 such as a needle, hook, barb, prong, or wedge configured to pierce the inner wall of the vessel and prevent migration of the intravascular filter 10 within the body. In use, each anchoring member 22 compresses against the inner wall of the blood vessel as a result of the outwardly directed force exerted by the filter legs 14.

The apical head 12 may include a magnetic element 24 that can be used to magnetically center and retrieve the intravascular filter 10 using a magnetic retrieval device. In certain embodiments, for example, the magnetic element 24 may include a bar magnet, magnetic ring, solenoid, or other suitable magnetic component incorporated into or otherwise forming the apical head 12. The magnetic element 24 can be configured to produce a magnetic field having a south pole and a north pole, corresponding, respectively, to a proximal end 26 and distal end 28 of the apical head 12. As is discussed in greater detail below, the formation of the magnetic field at the apical head 12 allows the intravascular filter 10 to be centered and retrieved within the blood vessel.

To produce the desired magnetic effect at the apical head 12, the magnetic element 24 may comprise a magnetic material having a magnetic flux density sufficient to attract or repel a similarly configured magnetic element on the magnetic retrieval device. Examples of suitable metallic magnetic materials may include Iron (Fe), Nickel (Ni), Cobalt (Co), Magnetite ($Fe_3O_4$), Neodymium-Iron-Boron (NdFeB), Aluminum-Nickel-Cobalt (AlNiCo), Samarium-Cobalt (SmCo), Awaruite ($Ni_3F$), Wairauite (CoFe), and alloys or composites thereof. It should be understood, however, that the magnetic element 24 is not limited to such materials. In other embodiments, for example, non-metallic materials such as vanadium-tetracyanoethylene, or thin-film polymeric materials such as thin film $V[TCNE]_x$ could be employed.

The magnetic element 24 can be configured to produce a magnetic field on either a continual basis or at discrete time intervals during the intravascular procedure. The particular characteristics of the magnetic element 24 will depend in part on the type of magnetic material(s) employed, the size and temperature of the magnetic element 24, the characteristics of the blood vessel and blood surrounding the magnetic element 24, and the magnetic properties of the magnetic retrieval device. In certain embodiments, for example, a ferromagnetic or ferrimagnetic material can be utilized to produce a spontaneous magnetic field at the apical head 12. The strength of the magnetic field produced can be controlled by selecting a material having a desired magnetic flux density and/or by controlling various physical parameters of the magnet element 24.

In certain embodiments, it may be desirable to exploit the material's thermal properties to produce a desired magnetic characteristic within the body. In those embodiments employing a ferromagnetic or ferrimagnetic material, for example, the Curie temperature ($T_c$) can be set at or about body temperature to permit the magnetic element 24 to normally function within the body without magnetizing. To induce magnetism within the magnetic element 24, a chilled saline solution can be delivered to the site of the magnetic element 24, causing the material to regain its magnetization characteristics and thus allowing the intravascular filter 10 to be magnetically retrieved. The magnetic element 24 can also be formed from materials having a high Remanence and a Currie temperature above that of body temperature.

In an alternative embodiment, the magnetic element 24 may comprise a paramagnetic material that becomes magnetized in response to an external magnetic field produced by the magnetic retrieval device. Unlike ferromagnetic/ferrimagnetic materials, paramagnetic materials do not exhibit a strong parallel atomic alignment in the absence of an external magnetic field. This property of the material may be useful in certain applications where continuous magnetization of the apical head 12 may interfere with the function and/or visualization of other devices inserted within the body, or where magnetization of the body is contraindicated.

Figure 2:
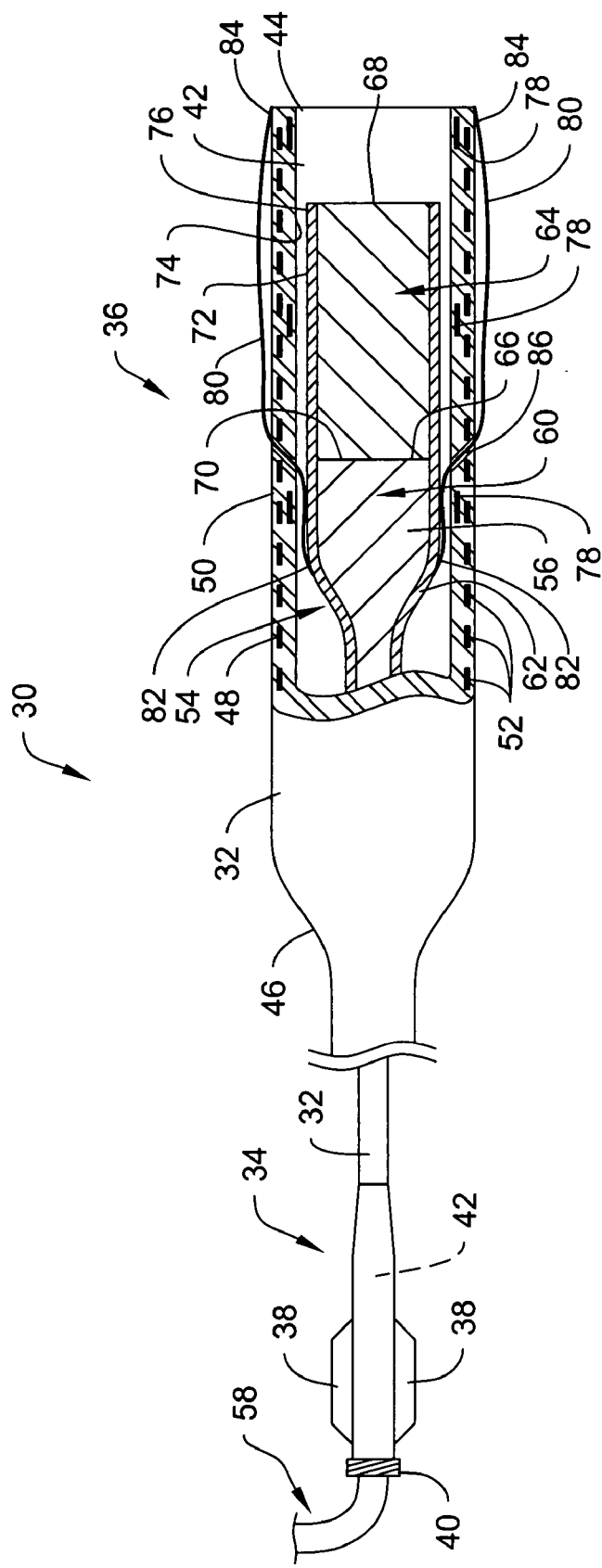
FIG. 2 is a partial cross-sectional view of a magnetic retrieval device in accordance with an illustrative embodiment of the present invention.

Referring now to FIG. 2, a magnetic retrieval device 30 in accordance with an illustrative embodiment of the present invention will now be described. As shown in FIG. 2, magnetic retrieval device 30 includes an elongated sheath 32 having a proximal section 34 and a distal section 36. The proximal section 34 of sheath 32 may include a number of gripping fins 38 that can be used to manipulate the magnetic retrieval device 30 from a location outside of the patient's body. A locking hub 40 disposed on the proximal section 34 of the sheath 32 may be provided to lock the positioning of the sheath 32 within the vasculature, if desired.

The sheath 32 may further define an interior lumen 42 configured to receive an intravascular device therein. The interior lumen 42 may extend through all or a portion of the sheath 32, terminating distally at a distal end 44 of the sheath 32. The sheath 32 may transition from a relatively low profile along the proximal section 34 of the sheath 32 to a larger profile along the distal section 36 to accommodate the collapsed intravascular device within the interior lumen 42. Such transition may occur, for example, at a flared region 46 of the sheath 32, wherein the profile of the sheath 32 expands slightly.

To provide additional axial and torsional rigidity, the magnetic retrieval device 30 may include a braid 48 or other suitable reinforcement member disposed within the tubular wall 50 of the sheath 32. The braid 48 may include a number of filaments 52 encased within or disposed adjacent to the tubular wall 50. The filaments 52 may be arranged generally in two sets of parallel helices wound in opposite directions about a common longitudinal axis that extends through the center of the magnetic retrieval device 30. The filaments 52 may intersect each other in an overlapping or interwoven fashion to permit the distal section 36 to radially expand when subjected to a compressive force. In the illustrative embodiment depicted in FIG. 2, the braid 48 extends along the entire length of the distal section 36, terminating proximally at or near the flared region 46. In other embodiments, however, the braid 48 may extend along only a portion of the distal section 36, or may extend further into all or a portion of the proximal section 34.

The magnetic retrieval device 30 may further include a magnetic retrieval mechanism 54 slidably disposed within the interior lumen 42 of the sheath 32. The magnetic retrieval mechanism 54 may include an elongated member 56 such as a wire or tube having a proximal section 58 and a distal section 60. The elongated member 56 may extend through all or a portion of the interior lumen 42 of the sheath 32, terminating proximally at a location outside of the body. In the illustrative embodiment of FIG. 2, for example, the elongated member 56 extends through the entire length of the magnetic retrieval device 30, terminating proximally at a location proximal to the hub 40. In other embodiments, however, the elongated member 56 may extend through only a portion of the interior lumen 42, exiting the sheath 32 through an exit port formed in the tubular wall 50. The elongated member 56 can be configured to slide and/or rotate within the interior lumen 42 of the sheath 32 by manipulating the proximal section 58 in an appropriate manner. A flared region 62 of the elongated member 56 transforms the profile of the elongated member 56 from a relatively small profile along the proximal section 58 to a relatively large profile along the distal section 60 thereof.

The distal section 60 of the elongated member 56 may further include a magnetic element 64 adapted to magnetically center and retrieve an intravascular device within the interior lumen 42 of the sheath 32. The magnetic element 64 may be configured similar to the magnetic element 24 described above with respect to FIG. 1, producing a magnetic field that can be used to magnetically attract the apical head 12 of the intravascular filter 10. In the illustrative embodiment depicted in FIG. 2, for example, the magnetic element 64 may comprise a bar magnet that produces a magnetic field having a south pole and a north pole corresponding, respectively, to a proximal end 66 and distal end 68 of the magnetic element 64.

The magnetic element 64 may be attached to or formed integrally with the distal section 60 of the elongated wire 56. In certain embodiments, for example, the magnetic element 64 may be attached to the elongated wire 56 via a butt joint 70. To maintain the elongated member 56 centrally within the interior lumen 42 while still permitting the elongated member 56 to slide and rotate within the sheath 32, the outer wall 72 of the elongated member 56 may have an outer diameter that is smaller than the inner diameter of the sheath inner wall 74. To reduce friction between the two surfaces 72,74, a thin lubricious layer or coating 76 may formed about the elongated member 56 and magnetic element 64.

A number of electromagnetic elements 78 disposed within the tubular wall 50 of the elongated sheath 12 can also be utilized to electromagnetically center and retrieve the intravascular device in conjunction with, or in lieu of, the magnetic element 64 of the elongated member 56. The electromagnetic elements 78 can be positioned within the distal section 36 of the elongated sheath 12 at a location adjacent to the magnetic element 64 such that, when energized via a number of electrical leads (not shown), a magnetic field is produced at the distal section 36. The electromagnetic elements 78 can be spaced apart from each other at equidistant intervals, as shown in FIG. 2, or can be spaced apart from each at various intervals.

To facilitate centering of the magnetic retrieval device 30 within the blood vessel, a number of wires 80 coupled to the elongated member 56 and sheath 32 can be configured to expand from a radially collapsed position to a radially enlarged position. Each wire 80 may extend from a first end 82 coupled to the elongated member 56 to a second end 84 coupled to the distal end 44 of the sheath 32. A number of openings 86 formed through the tubular wall 50 of the sheath 32 can be dimensioned to permit the wires 80 to expand outwardly when the elongated member 56 is moved relative to the sheath 32.

Figure 3:
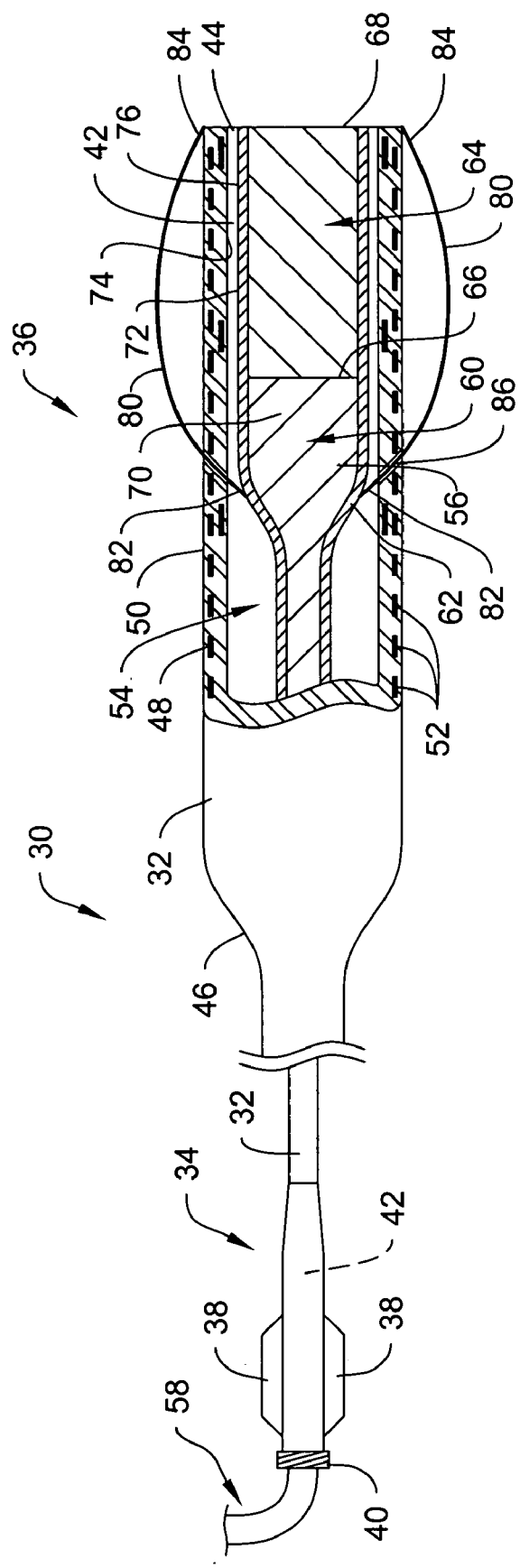
FIG. 3 is another partial cross-sectional view of the magnetic retrieval device of FIG. 2, showing the device in a second position.
Figure 4:
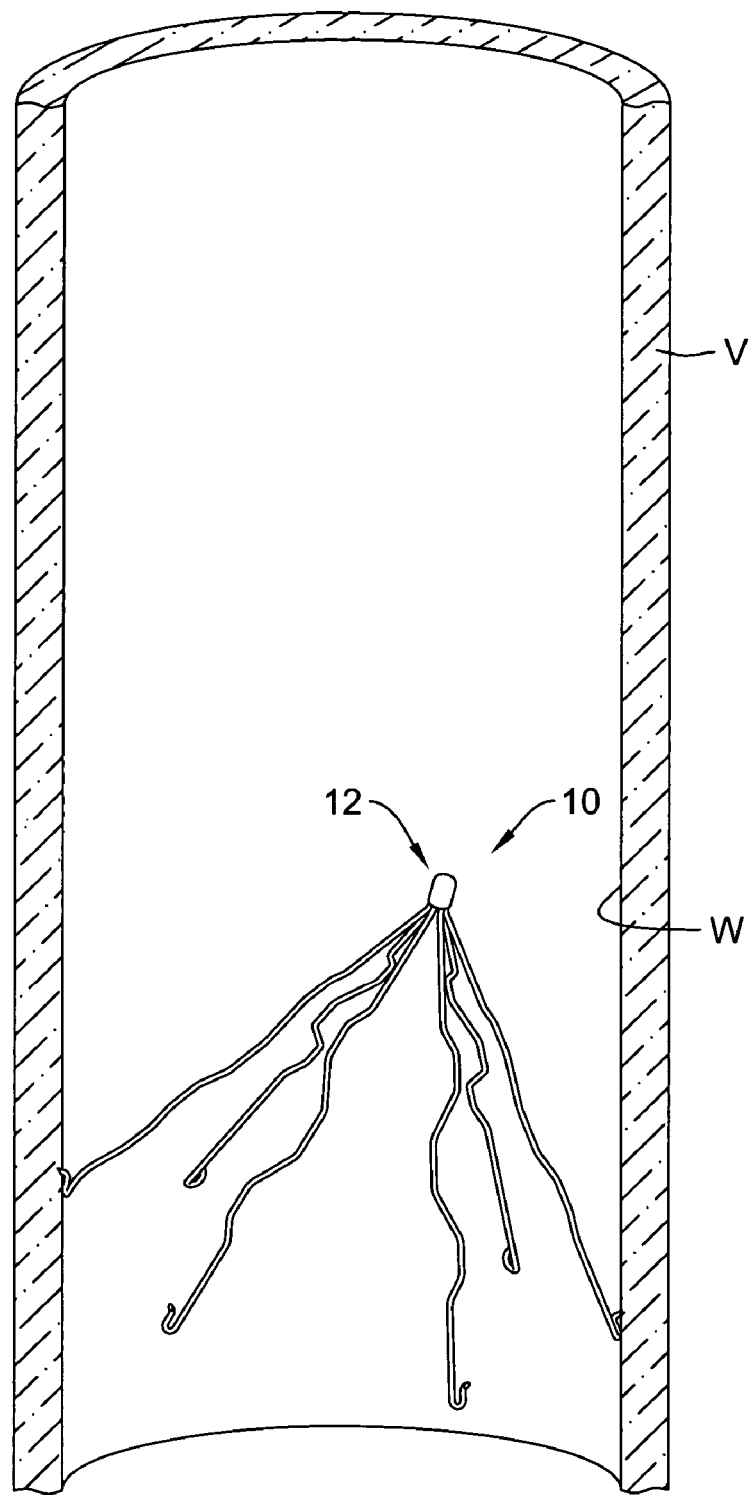
FIG. 4 is a partial cross-sectional view showing the intravascular filter of FIG. 1 disposed within a blood vessel.

In a generally collapsed position illustrated in FIG. 2, the elongated member 56 is disposed relative to the sheath 32 such that the magnetic element 64 is located proximally of the distal end 44. In this position, the wires 80 are disposed tightly against the outer surface of the sheath 32 to facilitate advancement of the magnetic retrieval device 30 through the vasculature. As can be seen in FIG. 3, however, the elongated member 56 can be advanced distally within the interior lumen 42 of the sheath 32, causing the wires 80 to radially expand to a second position to engage the vessel wall.

FIGS. 4-7 are partial cross-sectional views showing an illustrative method of using the magnetic retrieval device 30 of FIG. 2 to retrieve the intravascular filter 10 of FIG. 1 within a blood vessel. In a first position depicted in FIG. 4, intravascular filter 10 is shown deployed in an offset or tilted position within a blood vessel V. In this position, the apical head 12 of the intravascular filter 10 is misaligned with the central longitudinal axis of the blood vessel V. This misalignment can, in certain circumstances, make retrieval of the intravascular filter 10 using conventional retrieval devices more difficult since the physician must first align the retrieval device with the apical head 12 before the intravascular filter 10 can be collapsed therein.

Figure 5:
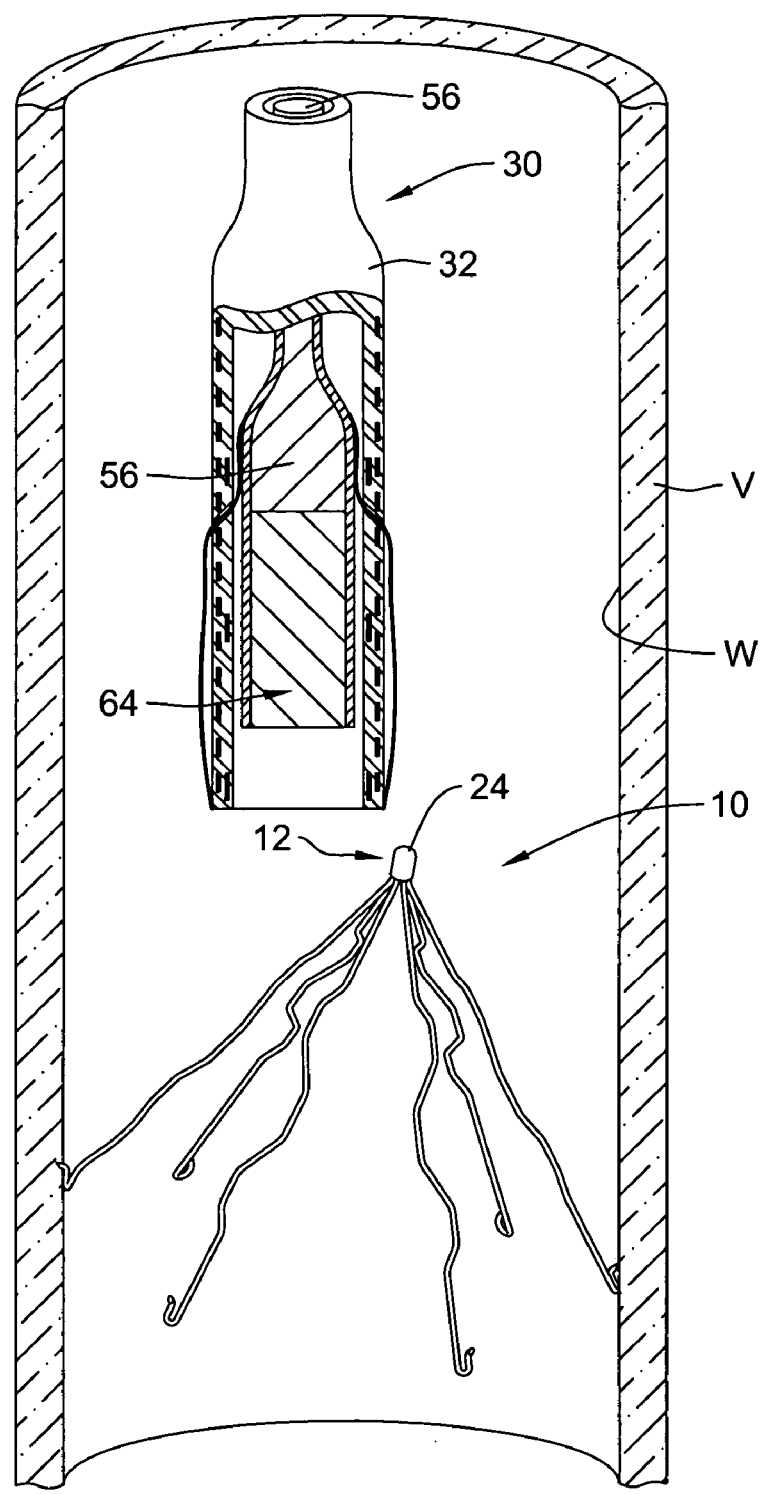
FIG. 5 is a partial cross-sectional view showing the magnetic retrieval device inserted within the blood vessel of FIG. 4.

To retrieve the intravascular filter 10 within the blood vessel V, the magnetic retrieval device 30 can be inserted percutaneously into the body, and advanced to a position adjacent to the apical head 12, as shown, for example, in FIG. 5. Insertion of the magnetic retrieval device 30 within the vasculature may be accomplished through either a femoral artery or jugular vein, depending on the orientation of the apical head 12 within the body. In the illustrative view depicted in FIG. 5, for example, the magnetic retrieval device 30 is shown inserted within a relatively large blood vessel (e.g. the inferior vena cava) via a jugular approach from a position above the implanted intravascular filter 10. Once inserted into the body, the magnetic retrieval device 30 can then be advanced through the body to the site of the intravascular filter 10. To facilitate advancement through the vasculature, a separate guide catheter and/or guidewire may be employed, consistent with standard practice in the art.

Figure 6:
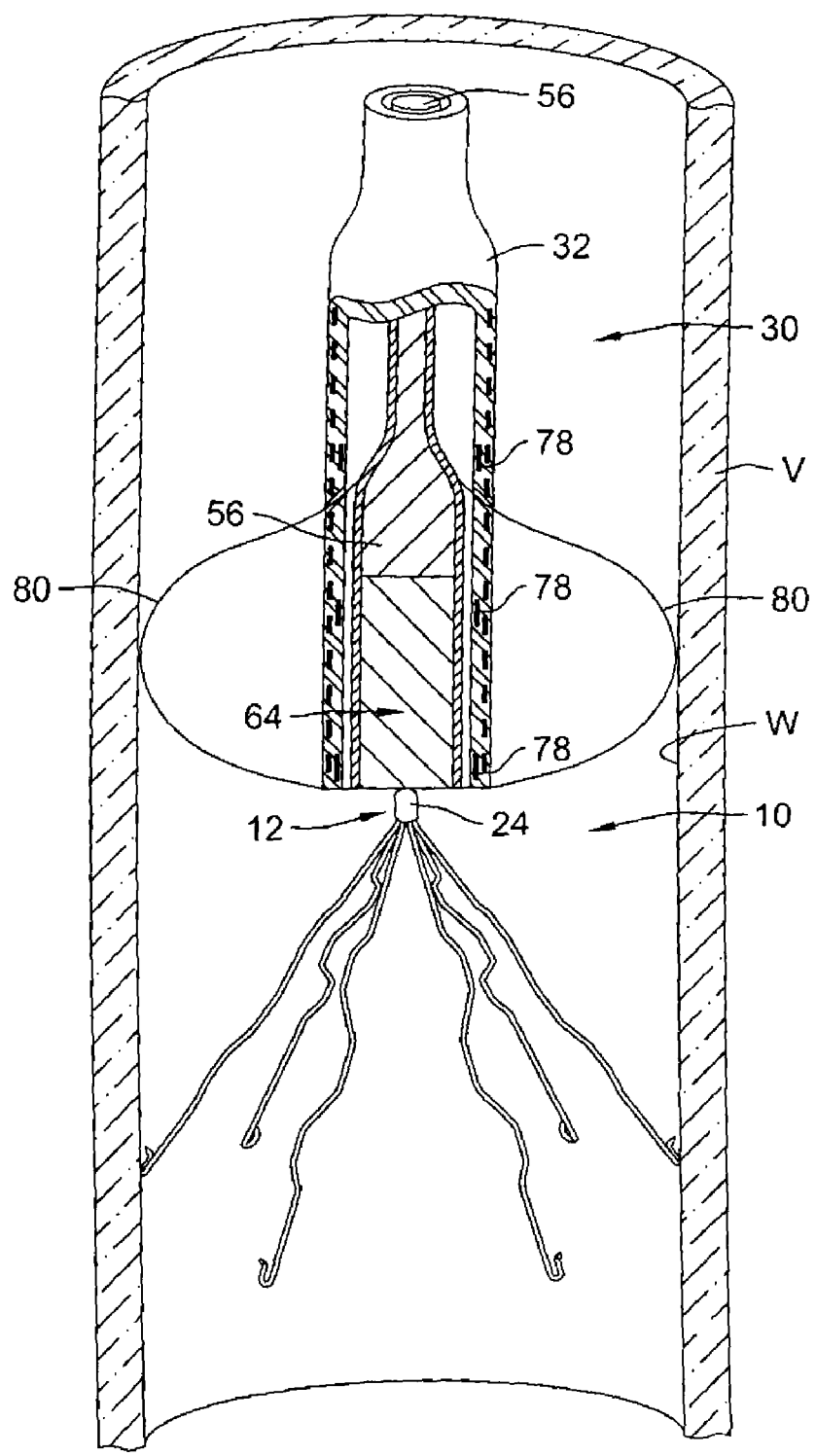
FIG. 6 is a partial cross-sectional view showing the magnetic retrieval device in a second position within the blood vessel of FIG. 4, wherein the magnetic element is shown advanced towards the apical head of the intravascular filter.

Once the magnetic retrieval device 30 has been advanced to the site of the intravascular filter 10, the physician may next advance the elongated member 56 distally towards the apical head 12 while holding the sheath 32 stationary, as shown, for example, in FIG. 6. As can be seen in FIG. 6, advancement of the elongated member 56 in this manner causes the wires 80 to expand and engage the wall W of the blood vessel V, centering the magnetic retrieval device 30 within the blood vessel V. Advancement of the elongated member 56 in this manner also forces the magnetic element 64 into close proximity with the magnetic element 24 of the intravascular filter 10. When this occurs, the opposite polarities of the magnetic elements 24,64 act to attract the apical head 12 towards the elongated member 56, magnetically coupling the two elements 24,64 together.

Figure 7:
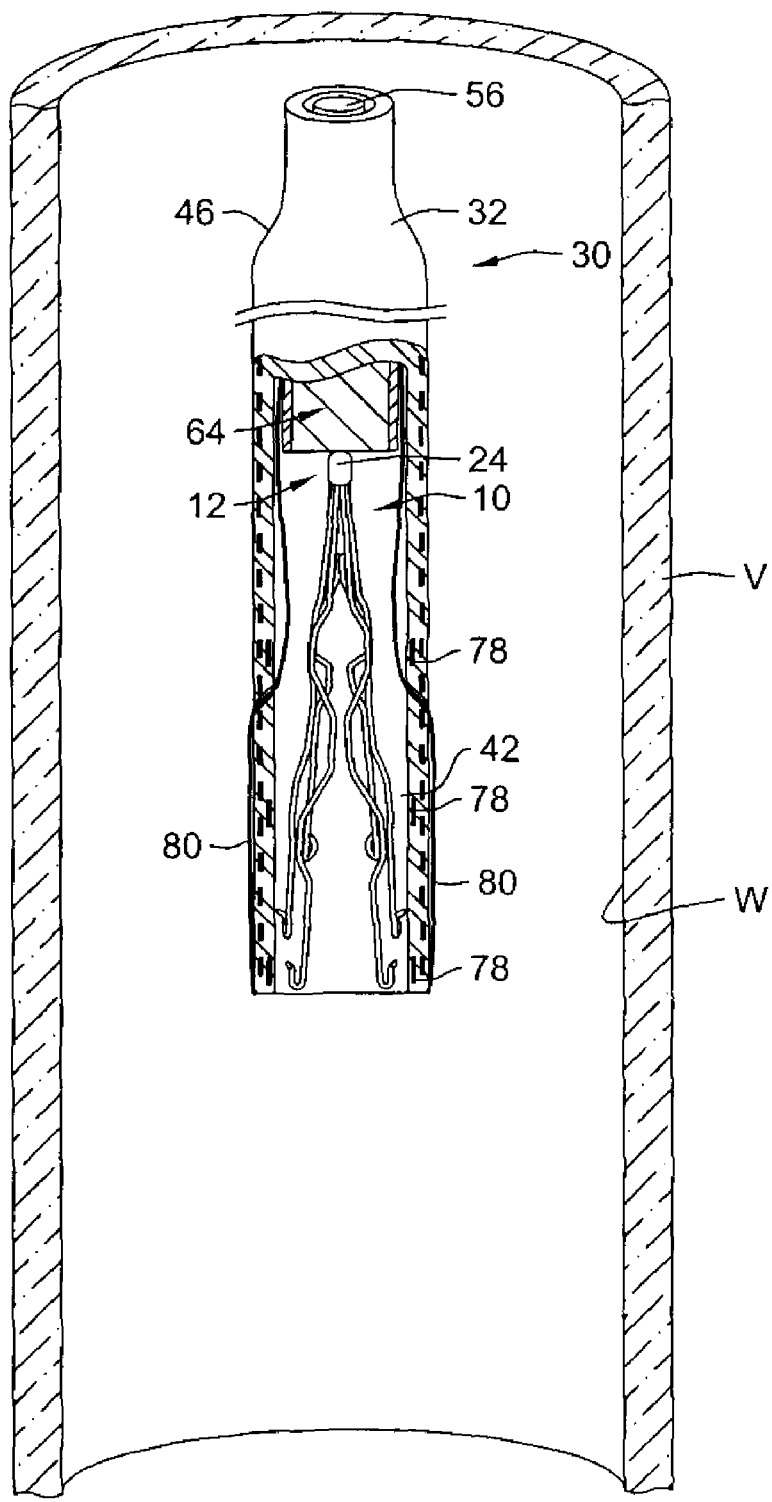
FIG. 7 is a partial cross-sectional view showing the magnetic retrieval device in a third position within the blood vessel of FIG. 4, wherein the intravascular filter is shown fully retracted within the magnetic retrieval device.

Once coupled together, the physician next retracts the elongated member 56 proximally, causing the intravascular filter 10 to detach from the vessel wall and retract into the interior lumen 42 of the sheath 32, as shown, for example, in FIG. 7. In those embodiments employing electromagnetic elements 78 an optional step of energizing the electromagnetic elements 78 can also be performed to increase the magnetic attraction force of the magnetic element 64. To prevent over-retraction of the intravascular filter 10 into the sheath 32, and to inform the physician that the intravascular filter 10 has been fully collapsed therein, the flared region 46 of the sheath 32 can be configured to engage the flared region 62 (see FIG. 2) of the elongated member 56, thereby acting as a proximal stop to prevent further axial movement of the elongated member 56 within the sheath 32. Once fully retracted within the interior lumen 42 of the sheath 32, the magnetic retrieval device 30 can then be withdrawn to remove the intravascular filter 10 from the body.

Figure 8:
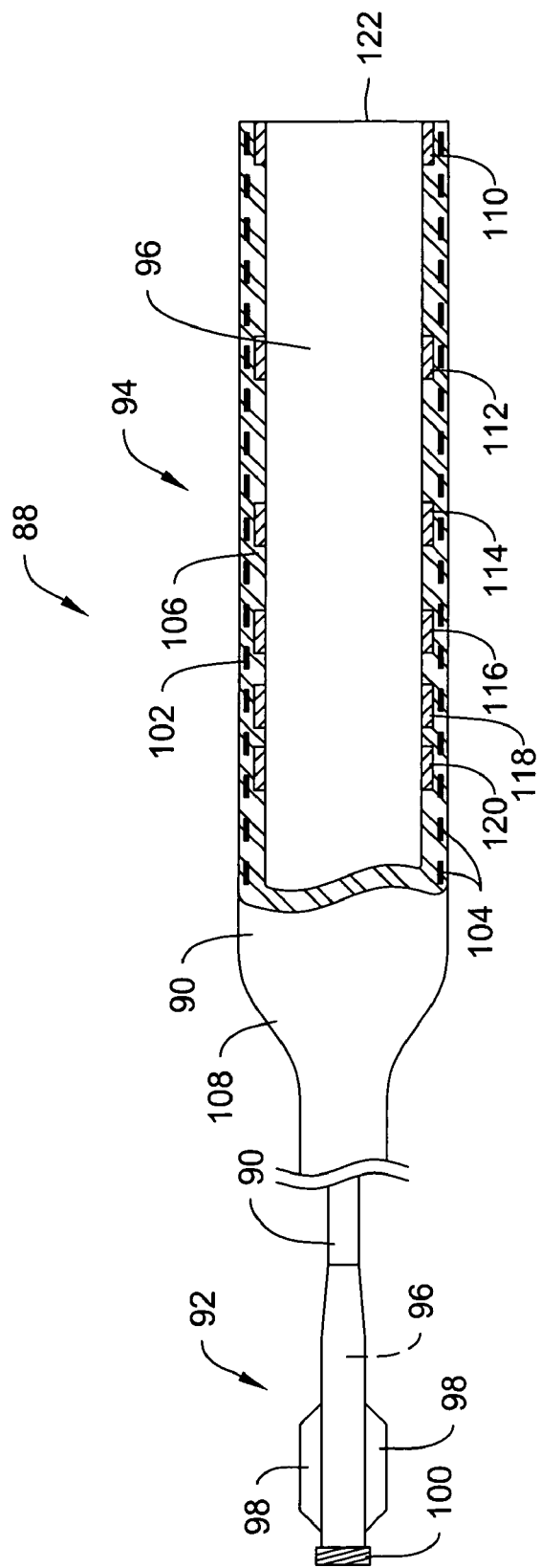
FIG. 8 is a partial cross-sectional view showing a magnetic retrieval device in accordance with another illustrative embodiment of the present invention.
Figure 9:
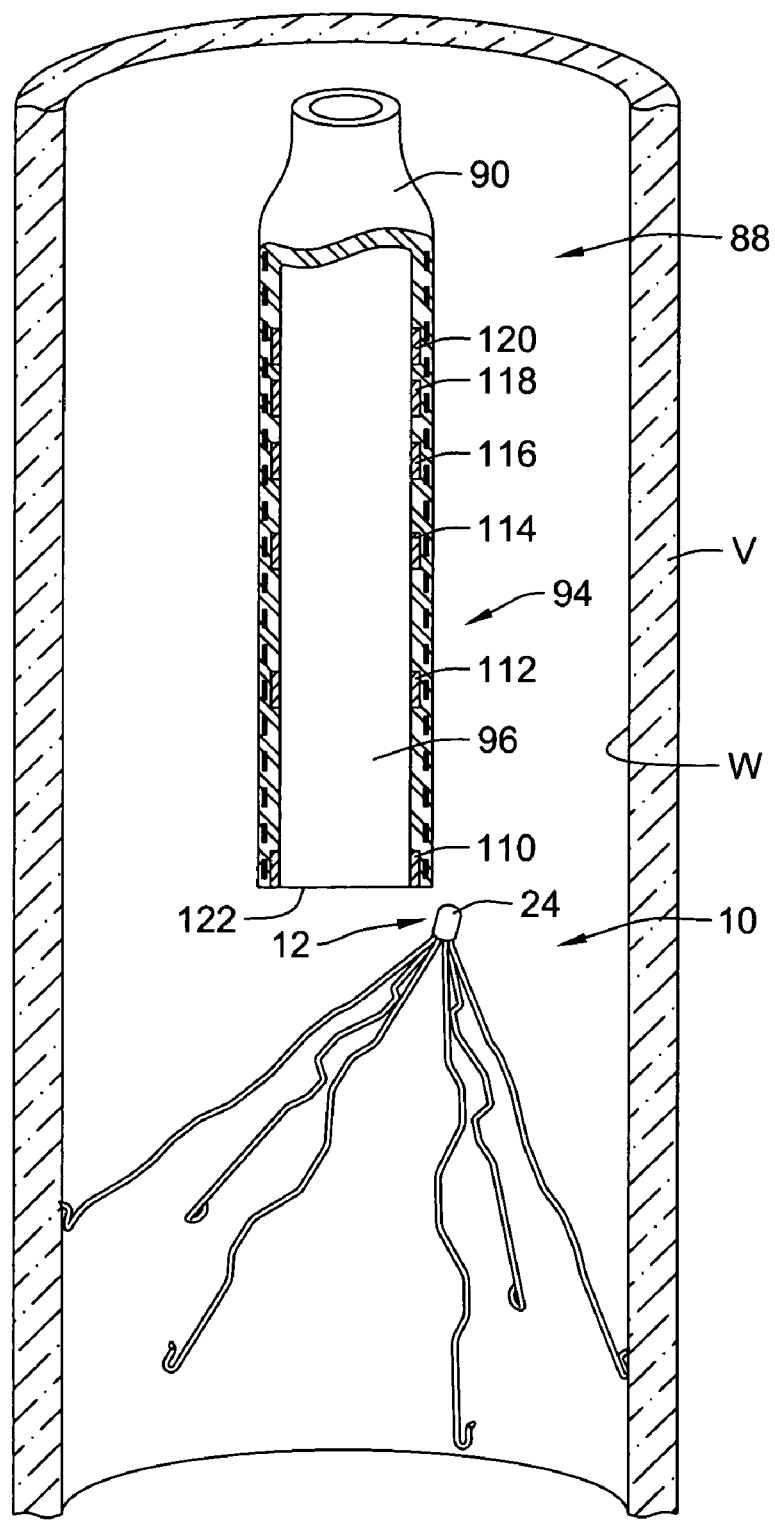
FIG. 9 is a partial cross-sectional view showing the magnetic retrieval device of FIG. 8 advanced to the site of an implanted intravascular filter.

FIG. 8 is a partial cross-sectional view showing a magnetic retrieval device 88 in accordance with another illustrative embodiment of the present invention employing one or more electromagnetic elements. Magnetic retrieval device 88 includes an elongated sheath 90 having a proximal section 92, a distal section 94, and an interior lumen 96 at least in part therethrough configured to receive an intravascular device. As with other embodiments described herein, the proximal section 92 of the sheath 90 may include a number of gripping fins 98 that can be used to manipulate the device from a location outside of the patient's body. A locking hub 100 disposed on the proximal section 92 of the sheath 90 may also be provided to lock the positioning of the sheath 90 along a guiding member such as a guidewire or guide catheter.

The sheath 90 may include a braid 102 or other suitable reinforcement means to provide additional axial and torsional rigidity to the magnetic retrieval device 88. The braid 102 may include a number of filaments 104 encased within or disposed adjacent to a tubular wall 106 of the sheath 90. Similar to the filaments 52 described above, the filaments 104 can be provided along all or a portion of the sheath 90, and can be configured to radially expand when subjected to a compressive force. A flared region 108 of the sheath 90 may also be provided to transition the sheath 90 from a relatively small profile along the proximal section 92 to a larger profile along the distal section 94 to accommodate the collapsed intravascular device within the interior lumen 96.

As can be further seen in FIG. 8, the magnetic retrieval device 88 may further include a number of electromagnetic elements 110,112,114,116,118,120 configured to electromagnetically center and retrieve the intravascular device. The electromagnetic elements 110,112,114,116,118,120 can be spaced apart from each other at variable intervals beginning with a first electromagnetic element 110 disposed at or near the distal end 122 of the sheath 90, and then extending proximally to a second electromagnetic element 112, a third electromagnetic element 114, and so forth. In certain embodiments, the spacing between each electromagnetic element 110,112,114,116,118,120 can decrease in the proximal direction along the sheath 90 to provide a greater magnetic field strength as the intravascular device is loaded further into the interior lumen 96 of the sheath 90.

The electromagnetic elements 110,112,114,116,118,120 may each comprise a magnetic ring or solenoid that can be used to produce a magnetic field when energized via a number of electrodes (not shown) disposed within the tubular wall 106. The electrode leads can be electrically connected to an electrical source located outside of the patient's body, which can be activated to deliver a current that can be used to induce a magnetic field. During retrieval, the electromagnetic elements 110,112,114,116,118,120 can each be selectively activated all at once, or at different intervals, to center and retrieve the intravascular device. In certain embodiments, for example, the electromagnetic elements 110,112,114,116,118,120 can be activated in cascading fashion beginning with the first electromagnetic element 110, and then activating each successive electromagnetic element as the intravascular device is further retrieved into the interior lumen 96 of the sheath 90.

While six electromagnetic elements are specifically illustrated in FIG. 8, it should be understood that a greater or lesser number of electromagnetic elements could be employed, if desired. Moreover, while the electromagnetic elements illustrated in FIG. 8 are spaced apart from each other with increasing concentration in the proximal direction, the electromagnetic elements may be arranged in some other desired fashion. In certain embodiments, for example, the electromagnetic elements can be arranged at equidistant intervals, similar to the illustrative magnetic retrieval device 30 of FIG. 2.

Figure 10:
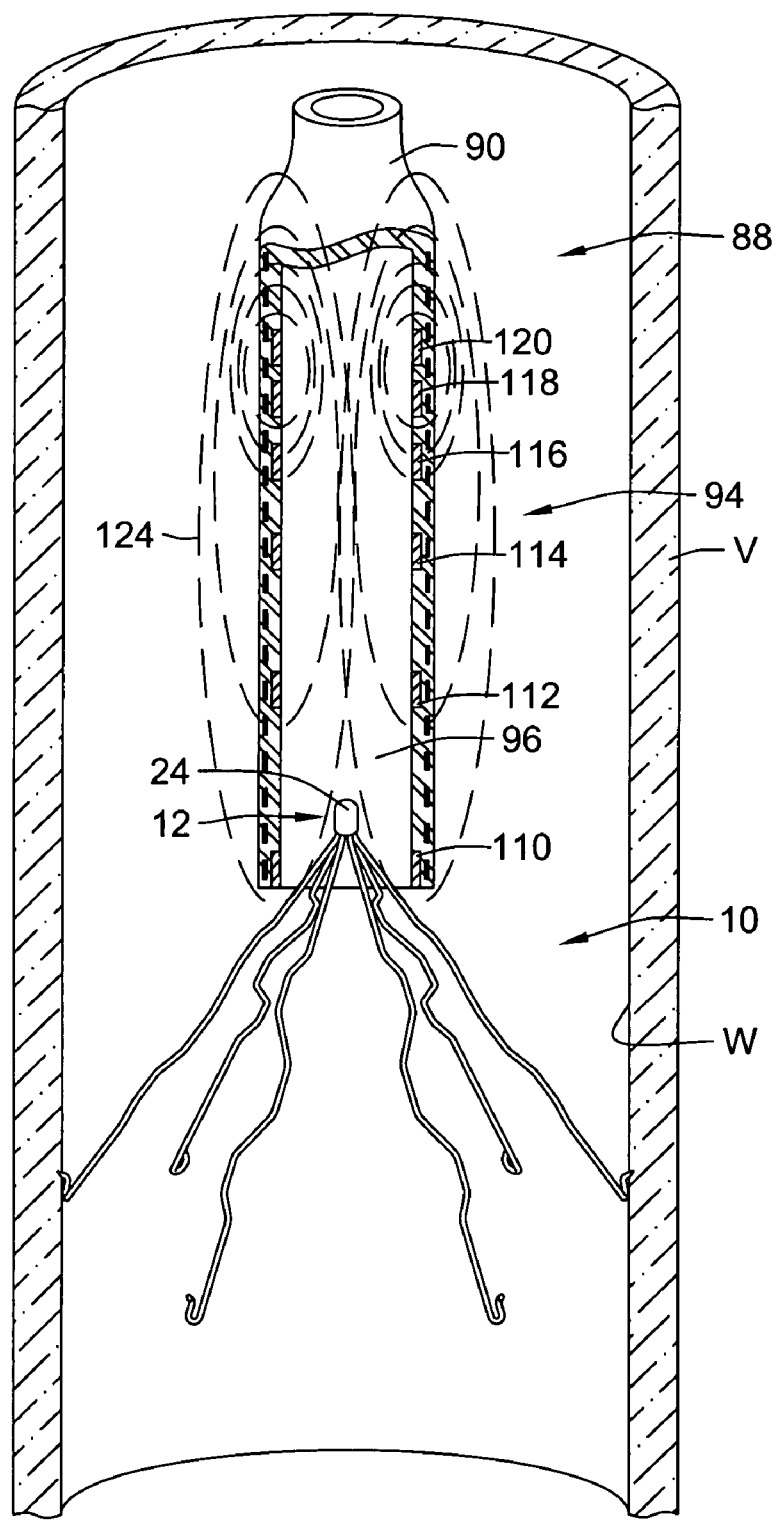
FIG. 10 is a partial cross-sectional view showing the magnetic retrieval device and intravascular filter of FIG. 9, wherein the intravascular filter is shown in a first position disposed within the magnetic retrieval device.
Figure 11:
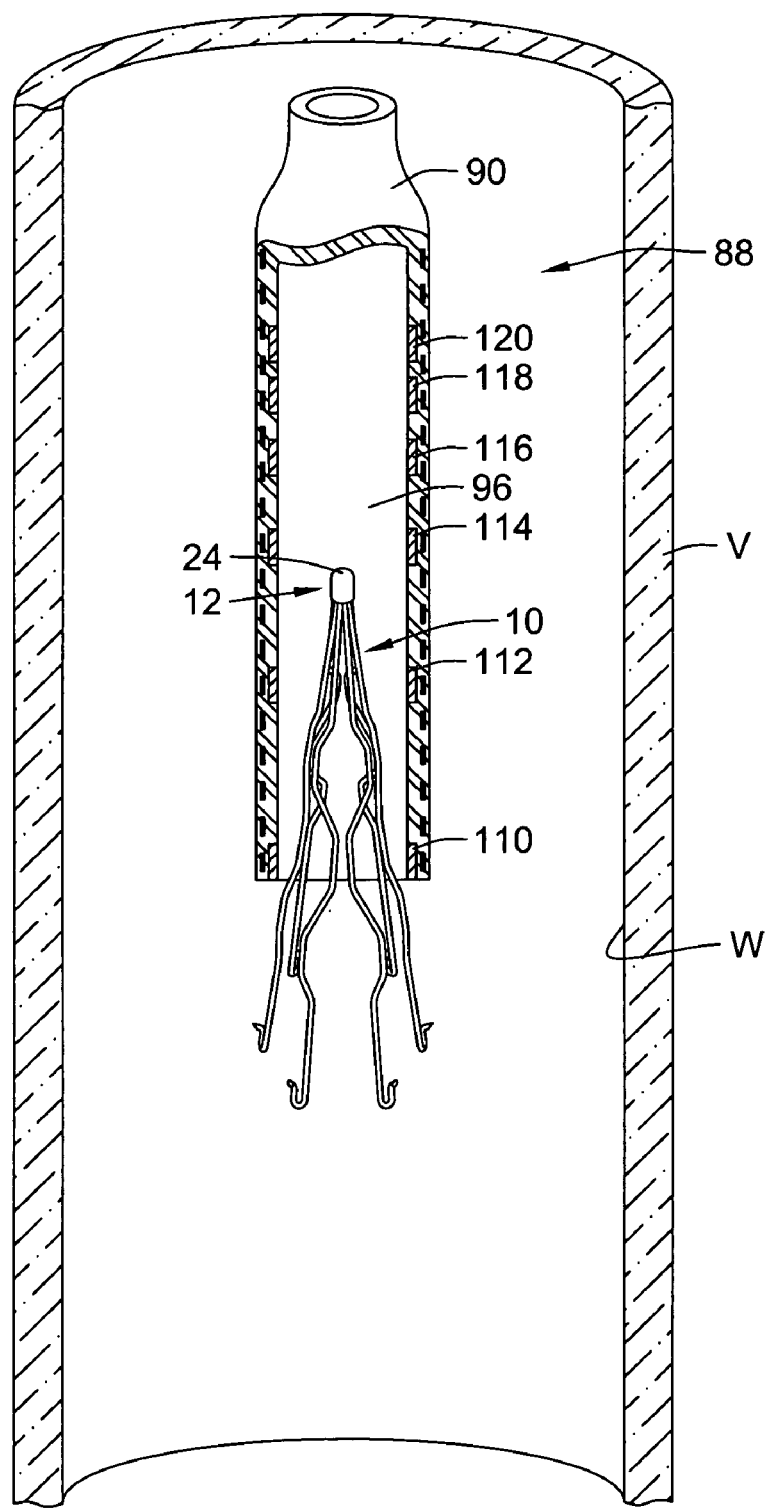
FIG. 11 is a partial cross-sectional view showing the magnetic retrieval device intravascular filter of FIG. 9, wherein the intravascular filter is shown in a second position disposed within the magnetic retrieval device.

Referring now to FIGS. 9-12, an illustrative method of centering and retrieving an intravascular device using the magnetic retrieval device 88 of FIG. 8 will now be described. In a first position illustrated in FIG. 9, magnetic retrieval device 88 is shown advanced within a blood vessel V to a location adjacent to an implanted intravascular device (e.g. intravascular filter 10). With the distal end 122 of the sheath 90 advanced adjacent to the apical head 12, one or more of the electromagnetic elements can then activated, inducing a magnetic field at the distal section 94 of the sheath 90 having a strength sufficient to detach the intravascular filter 10 from the vessel wall W. As illustrated in FIG. 10, for example, the activation of one or more of the electromagnetic elements produces a magnetic field 124 (represented generally by dashed lines) that causes the magnetic element 24 of the apical head 12 to align with the central longitudinal axis of the magnetic retrieval device 88 and retract into the interior lumen 96 of the sheath 90.

Once the apical head 12 has been drawn into the interior lumen 96 beyond the first electromagnetic element 110, the activation of the other electromagnetic elements 112,114, 116,118,120 can be configured to further drawn the intravascular filter 10 into the interior lumen 96 of the sheath 90. In a third position illustrated in FIG. 11, for example, the intravascular filter 10 is shown further retracted into the interior lumen 96, with the apical head 12 being advanced to a subsequent position located proximally of the second electromagnetic element 112. To aid in retracting the filter inwardly in this manner, the flow of current delivered to the first electromagnetic element 110 can be reversed, inducing a magnetic field that can be used to repel the apical head 12 further proximally into the interior lumen 96 of the sheath 80.

Figure 12:
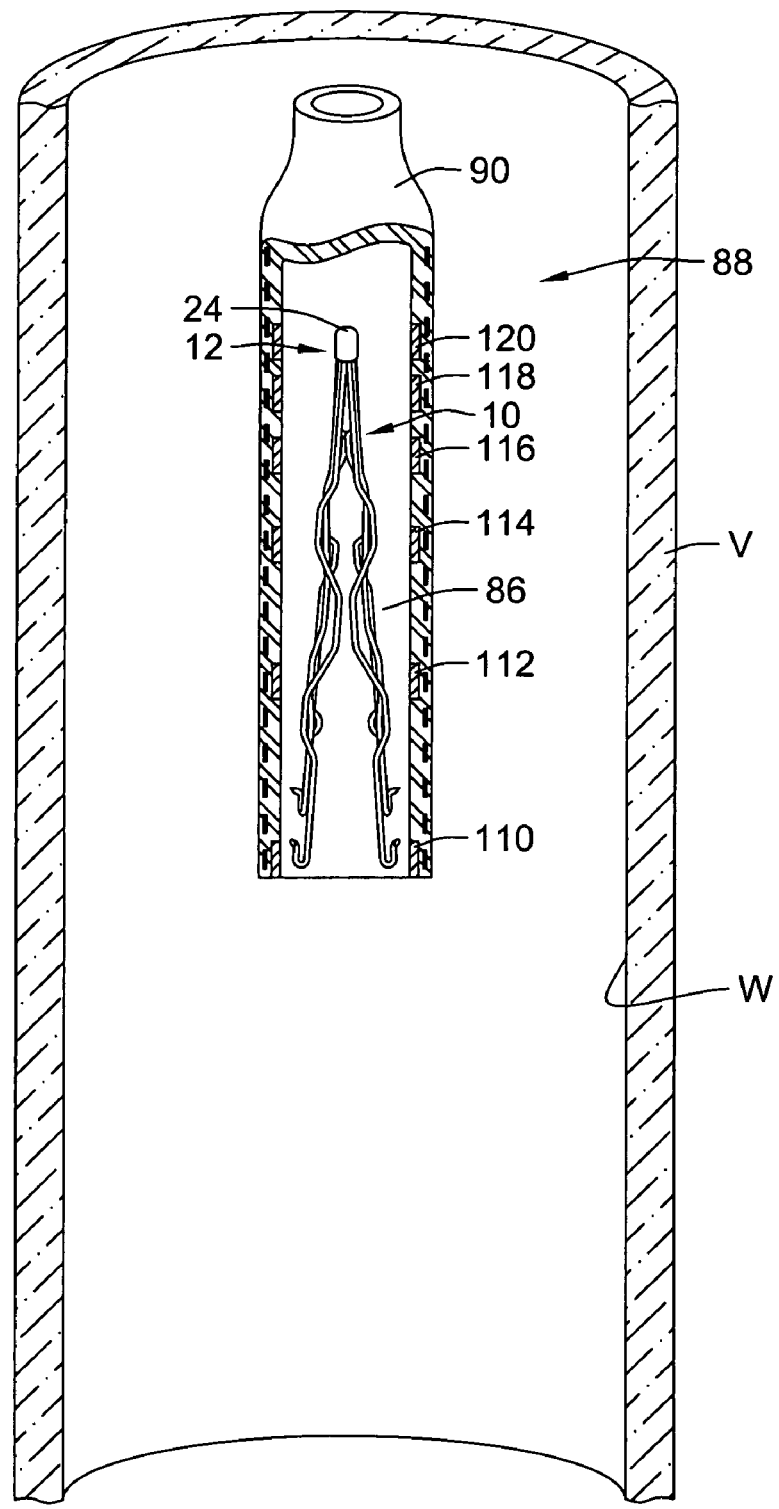
FIG. 12 is a partial cross-sectional view showing the magnetic retrieval device and intravascular filter of FIG. 9, wherein the intravascular filter is shown in a third position fully retracted within the magnetic retrieval device.

Further retraction of the intravascular filter 10 within the interior lumen 96 of the sheath 90 causes the intravascular filter 10 to collapse and assume a retrieval position, as shown, for example, in FIG. 12. Once the intravascular filter 10 has been fully retracted into the interior lumen 96, the physician can then withdraw the magnetic retrieval device 88 to remove the intravascular filter 10 from the body.

Figure 13:
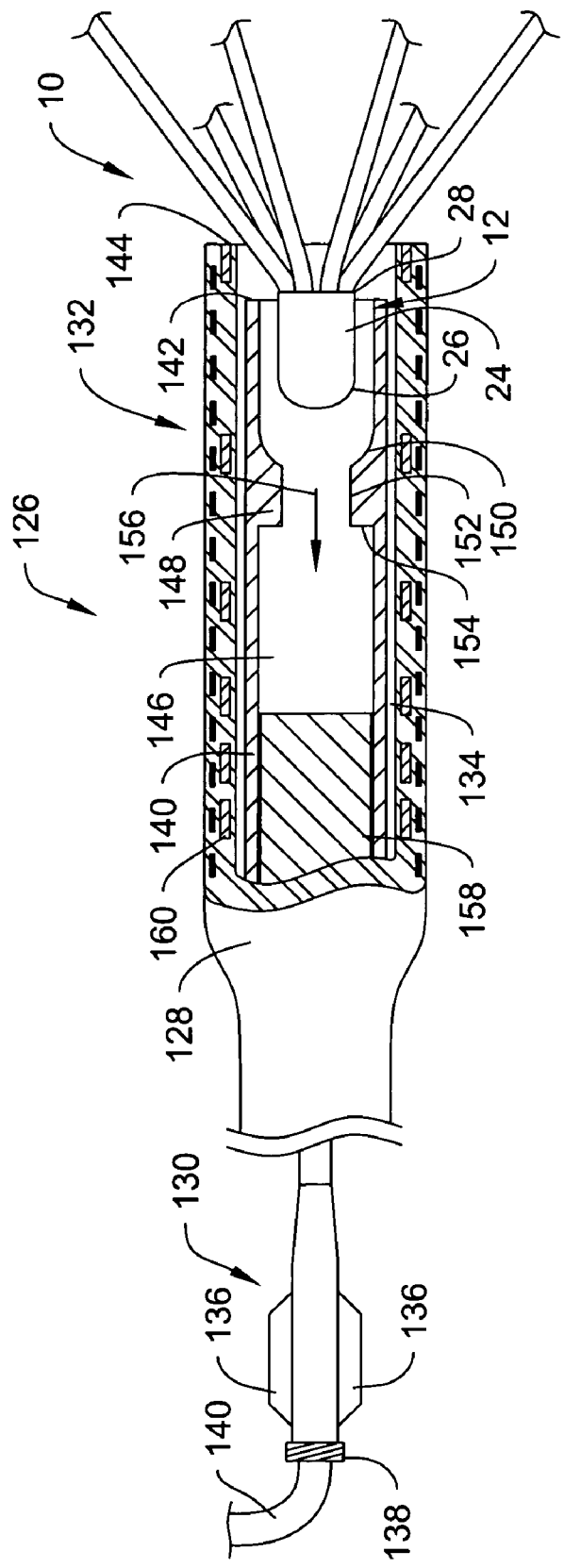
FIG. 13 is a partial cross-sectional view showing a magnetic retrieval device in accordance with another illustrative embodiment of the present invention employing a locking mechanism.

FIG. 13 is a partial cross-sectional view showing a magnetic retrieval device 126 in accordance with another illustrative embodiment of the present invention employing a locking mechanism. Magnetic retrieval device 126 includes an elongated sheath 128 having a proximal section 130, a distal section 132, and an interior lumen 134 at least in part therethrough configured to receive an intravascular device such as intravascular filter 10. The proximal section 130 of the sheath 128 may include a number of gripping fins 136 that can be used to manipulate the magnetic retrieval device 126 from a location outside of the patient's body. Other features such as a locking hub 138 may also be provided, if desired.

The magnetic retrieval device 126 may further include an inner tubular member 140 configured to lock onto the apical head 12 of the intravascular filter 10. The inner tubular member 140 can be dimensioned to slide and rotate within the interior lumen 134 of the sheath 128, allowing a distal end 142 of the inner tubular member 140 to be advanced distally beyond the distal end 144 of the sheath 128 during retrieval.

The inner tubular member 140 may define an interior lumen 146 adapted to slidably receive the apical head 12 of the intravascular filter 10. An internal projection 148 extending inwardly within the interior lumen 146 forms a locking mechanism that can be used to secure the apical head 12 to the inner tubular member 140. In the illustrative embodiment of FIG. 13, for example, the internal projection 148 may include a sloping portion 150, a constant diameter portion 152, and a shoulder portion 154. In use, the sloping and constant diameter portions 150,152 can be configured flex or bend slightly to permit the apical head 12 to move within the interior lumen 146 in only the proximal direction, as indicated generally by the arrow 156. Once advanced beyond the internal projection 148, the shoulder portion 154 can be configured to engage the proximal end 28 of the apical head 12, thereby securing the intravascular filter 10 to the magnetic retrieval device 126.

Retrieval of the intravascular filter 10 can be accomplished in a manner similar to that described herein. A magnetic element 158 slidably disposed within the interior lumen 146 can be advanced to a location adjacent to the shoulder 154. The magnetic element 158 can be configured to produce a magnetic field having a polarity opposite that of the magnetic element 24, causing apical head 12 to be drawn proximally within the interior lumen 146 beyond the internal projection 148. In certain embodiments, a number of electromagnetic elements 160 disposed within the sheath 128 can also be utilized to magnetically attract the magnetic element 24, causing it to move proximally within the interior lumen 146.

With the apical head 12 secured to the inner tubular member 140, the intravascular filter 10 can then be withdrawn into the interior lumen 134 of the sheath 128 by advancing the sheath 128 distally while holding the inner tubular member 140 stationary, or alternatively, by advancing the inner tubular member 140 proximally while holding the sheath 128 stationary. Once collapsed therein, the magnetic retrieval device 126 and accompanying intravascular filter 10 can then be removed from the body, if desired.

Figure 14:
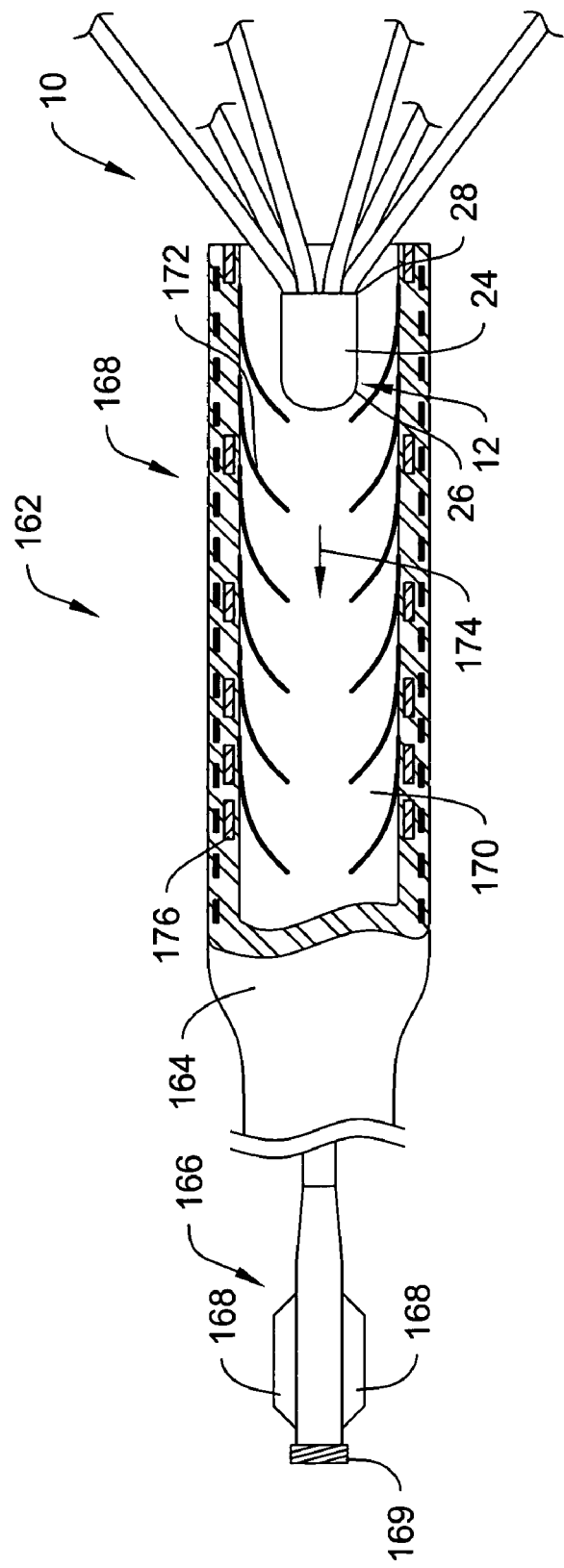
FIG. 14 is a partial cross-sectional view showing a magnetic retrieval device in accordance with another illustrative embodiment of the present invention employing a locking mechanism.

FIG. 14 is a partial cross-sectional view showing a magnetic retrieval device 162 in accordance with another illustrative embodiment of the present invention employing a locking mechanism. Magnetic retrieval device 162 includes an elongated sheath 164 having a proximal section 166, a distal section 168, and an interior lumen 170 at least in part therethrough configured to receive an intravascular device such as intravascular filter 10. As with other embodiments herein, the proximal section 166 of the sheath 164 may include a number of gripping fins 168 that can be used to manipulate the magnetic retrieval device 162 from a location outside of the patient's body, and a locking hub 169 to lock the magnetic retrieval device 162 to a guiding member such as a guidewire.

A number of inwardly projecting fingers 172 extending into the interior lumen 170 of the sheath 164 can be configured to lock to the apical head 12 of the intravascular filter 10 during retrieval. The inwardly projecting fingers 172 can be configured to displace and permit movement of the apical head 12 only in response to movement in the direction indicated generally by arrow 174.

Retrieval of the intravascular filter 10 can be accomplished in a manner similar to that described herein. One or more electromagnetic elements 176 disposed within the distal section 168 of the sheath 164 can be configured to produce a magnetic field that magnetically attracts the intravascular filter 10 into the interior lumen 170 of the sheath 64. As the apical head 12 is advanced further into the interior lumen 170, each of the inwardly projecting fingers 172 can be configured to displace to permit the intravascular filter 10 to be secured further within the interior lumen 170 of the sheath 164. Once collapsed therein, the magnetic retrieval device 162 and accompanying intravascular filter 10 can then be removed from the body, if desired.

Figure 15:
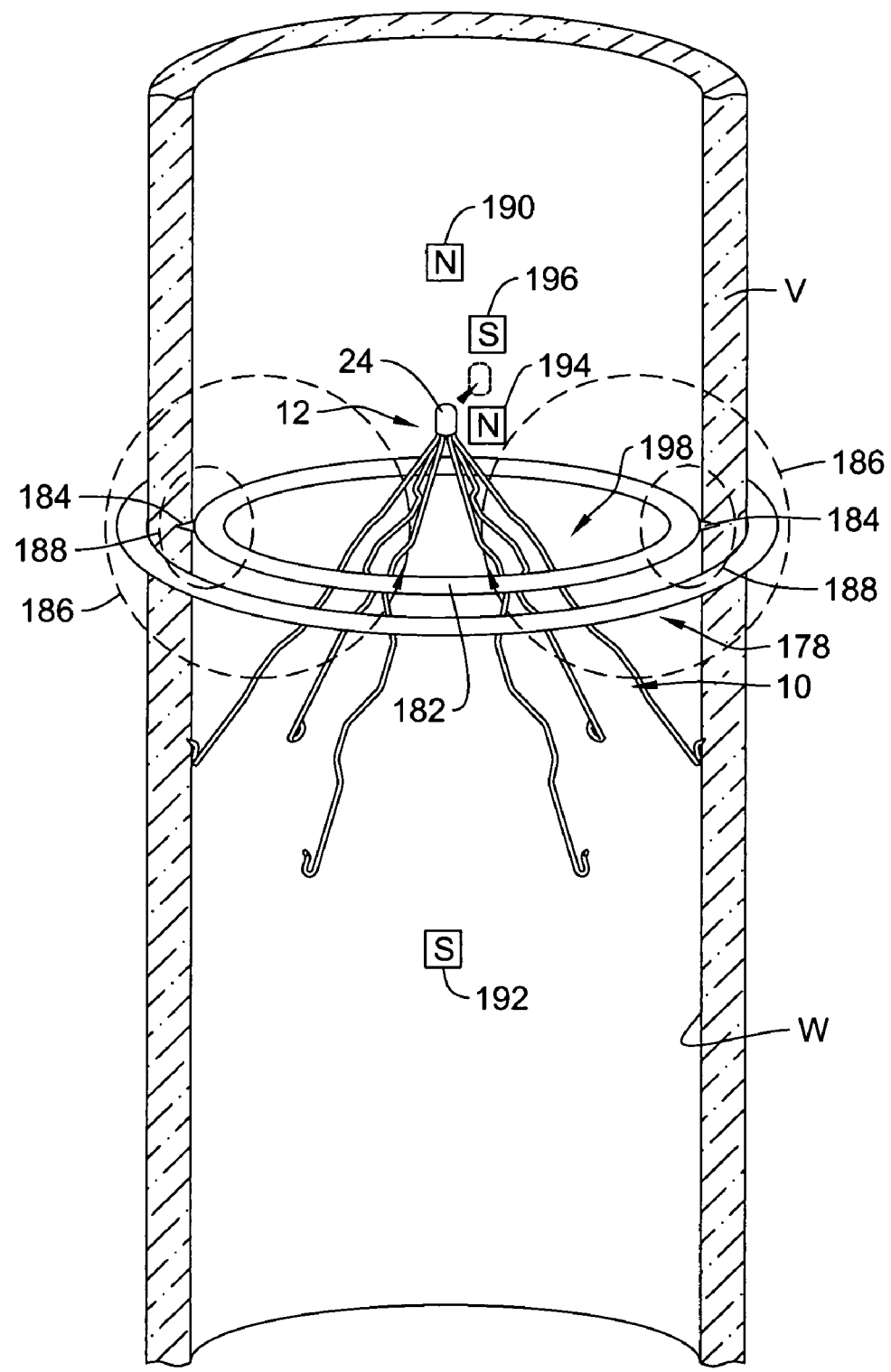
FIG. 15 is a partial cross-sectional view showing a number of magnetic centering rings disposed within a blood vessel.

FIG. 15 is a partial cross-sectional view showing a magnetic centering device 178 for use in centering an intravascular device (e.g. intravascular filter 10) within a blood vessel V. As shown in FIG. 15, the magnetic centering device 178 can comprise an outer magnetic ring 180 that can be placed about the outer wall of the blood vessel V, and an optional inner magnetic ring 182 that can be expanded and supported within the interior of the blood vessel V. The inner and outer magnetic rings 180,182 can both be configured for either permanent or temporary insertion within the blood vessel V. In the illustrative embodiment of FIG. 15, for example, a number of anchoring members 184 are shown disposed about the outer periphery of the inner magnetic ring 182 to aid in securing the inner magnetic ring 182 to the internal wall W of the blood vessel V.

The outer magnetic ring 182 can be configured to produce a magnetic field within the blood vessel V that can be used to repel the magnetic element 24 of the apical head 12 towards the center of the blood vessel V. In certain embodiments, for example, the outer magnetic ring 182 may comprise an electromagnetic element such as a solenoid that can be energized to produce a first magnetic field 186 within the blood vessel V. The inner magnetic centering ring 182, in turn, can comprise a paramagnetic element that, when energized via a charge from the outer magnetic centering ring 180, produces a second magnetic field 188 within the blood vessel V. When energized in this manner, the outer and inner magnetic rings 180,182 combine to produce a magnetic dipole having a north pole 190 and south pole 192. The magnetic element 24 of the apical head 12, in turn, can have a north pole 194 and south pole 196 configuration that is opposite of that produced by the outer and inner magnetic rings 180,182.

An illustrative method of centering the intravascular filter 10 using the magnetic centering device 178 may include the steps of implanting the outer and inner magnetic rings 180, 182 at a target location of the blood vessel V, advancing the intravascular filter 10 to a position such that the apical head 12 is located proximal the interior 198 of the inner magnetic centering ring 182, and then deploying the intravascular filter 10 within the blood vessel V. As the intravascular filter 10 is deployed, the repulsive force produced by the magnetic rings 180,182 causes the apical head 12 to align centrally within the interior 198 of the inner magnetic centering ring 182, preventing the intravascular filter 10 from becoming tilted or offset within the blood vessel V.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A magnetic retrieval device for retrieving an intravascular device disposed within a body lumen, comprising:
   an elongated tubular sheath comprising at least one electromagnetic element, the elongated tubular sheath having a proximal section, a distal section, and an interior lumen at least in part therethrough, the elongated tubular sheath including a wall, said wall having an inner surface, an outer surface, and a body therebetween;
   a magnetic retrieval mechanism adapted to magnetically retrieve the intravascular device; and
   a number of wires, each wire extending from a first end fixedly coupled to the magnetic retrieval mechanism to a second end fixedly coupled to a distal end of the elongated tubular sheath;
   wherein the magnetic retrieval mechanism is disposed within the interior lumen;
   wherein the number of wires pass through the wall of the elongated tubular sheath.

2. The magnetic retrieval device of claim 1, wherein the magnetic retrieval mechanism comprises an elongated member and at least one magnetic element.

3. The magnetic retrieval device of claim 2, wherein each magnetic element comprises a bar magnet.

4. The magnetic retrieval device of claim 2, wherein each magnetic element comprises a magnetic ring or solenoid.

5. The magnetic retrieval device of claim 1, wherein the magnetic retrieval mechanism includes a magnetic element and an inner tubular member slidably disposed within the interior lumen of the elongated sheath.

6. The magnetic retrieval device of claim 5, further comprising a locking mechanism for securing the intravascular device to the magnetic retrieval device.

7. A system for magnetically retrieving an intravascular filter disposed within a body lumen, comprising:
   an intravascular filter device including an expandable frame structure and at least one magnetic element; and
   a magnetic retrieval device adapted to magnetically retrieve the intravascular filter device, the magnetic retrieval device including a magnetic retrieval mechanism and a tubular elongated sheath comprising at least one electromagnetic element, the tubular elongated sheath including a wall, said wall having an inner surface, an outer surface, and a body therebetween;
   wherein the tubular elongated sheath further includes an interior lumen therethrough, the interior lumen defined by the inner surface;
   a number of wires, each wire extending from a first end fixedly coupled to the magnetic retrieval mechanism to a second end fixedly coupled to a distal end of the tubular elongated sheath;
   wherein the number of wires are configured to extend through the wall of the tubular elongated sheath and to expand from a radially collapsed position to a radially expanded position as the magnetic retrieval mechanism is moved relative to the tubular elongated sheath.

8. The system of claim 7, wherein the magnetic retrieval mechanism includes an elongated member operatively coupled to at least one magnetic element.

9. The system of claim 7, wherein the magnetic retrieval mechanism includes another magnetic element and an inner tubular member slidably disposed within the interior lumen of the sheath.

10. The system of claim 7, wherein the intravascular filter device includes a plurality of elongated filter legs operatively coupled to an apical head.

11. The system for of claim 10, wherein each of said plurality of filter legs is biased to expand from a substantially straight position to an outswept position when deployed in a blood vessel.

12. The system of claim 11, wherein the intravascular filter device further comprises anchoring means for securing the intravascular filter device to the wall of the blood vessel.

13. The system of claim 7, wherein the magnetic element of the intravascular filter device is configured to produce a magnetic field.

14. The system of claim 7, wherein the magnetic element of the intravascular filter device comprises a bar magnet.

15. The system of claim 7, wherein the magnetic element of the intravascular filter device comprises a magnetic ring or solenoid.

16. The system of claim 7, wherein the magnetic element of the intravascular filter device includes a ferromagnetic material.

17. The system of claim 16, wherein said ferromagnetic material of the intravascular filter device has a Curie temperature at or about body temperature.

18. The system of claim 7, wherein the magnetic element of the intravascular filter device includes a paramagnetic material.

* * * * *